(12) United States Patent
Sekine et al.

(10) Patent No.: US 7,551,273 B2
(45) Date of Patent: Jun. 23, 2009

(54) MASK DEFECT INSPECTION APPARATUS

(75) Inventors: Akihiko Sekine, Itabashi-ku (JP);
Ikunao Isomura, Kawasaki (JP);
Toshiyuki Watanabe, Kawasaki (JP);
Shinji Sugihara, Kawasaki (JP); Riki Ogawa, Kawasaki (JP)

(73) Assignee: Kabushiki Kaisha TOPCON, Tokyo (JP)

(*) Notice: Subject to any disclaimer, the term of this patent is extended or adjusted under 35 U.S.C. 154(b) by 0 days.

(21) Appl. No.: 12/081,852

(22) Filed: Apr. 22, 2008

(65) Prior Publication Data

US 2008/0204723 A1    Aug. 28, 2008

Related U.S. Application Data

(63) Continuation of application No. 11/083,202, filed on Mar. 18, 2005, now Pat. No. 7,379,176.

(30) Foreign Application Priority Data

Mar. 22, 2004    (JP) ............................... 2004-081767

(51) Int. Cl.
*G01N 21/00* (2006.01)
(52) U.S. Cl. ............. 356/237.5; 356/237.1; 356/237.2; 356/237.4

(58) Field of Classification Search ... 356/237.1–237.6, 356/388–395, 432–433, 368, 429, 30; 250/559.2, 250/559.34, 559.36–559.39, 559.4, 559.45, 250/306; 382/149, 255, 141, 218, 144, 148, 382/199, 256–275, 293
See application file for complete search history.

(56) References Cited

U.S. PATENT DOCUMENTS

| 6,100,970 A * | 8/2000 | Yoshino et al. ........... 356/237.6 |
| 6,175,645 B1 * | 1/2001 | Elyasaf et al. .............. 382/147 |
| 2004/0114824 A1 * | 6/2004 | Ogawa et al. ................ 382/255 |

FOREIGN PATENT DOCUMENTS

| JP | 10-097053 A | 4/1998 |
| JP | 2002-039960 A | 2/2002 |
| JP | 2003-209043 A | 7/2003 |

* cited by examiner

*Primary Examiner*—Gregory J Toatley, Jr.
*Assistant Examiner*—Tri T Ton
(74) *Attorney, Agent, or Firm*—Buchanan Ingersoll & Rooney PC

(57) ABSTRACT

The mask defect inspection apparatus including an illumination optical system for illuminating a mask on which a pattern is formed; an objective lens facing the mask; at least a pair of detection optical systems having a detection sensor for obtaining an image of the pattern, respectively, and which receive illumination light from illumination areas different from each other through the objective lens, respectively; and focusing changing means for changing a position of focusing between sites of the pattern in a film-thickness direction of the mask and the pattern images obtained by the detection sensors, such that the pattern images obtained by the detection sensors are changed corresponding to the film-thickness direction of the mask.

17 Claims, 11 Drawing Sheets

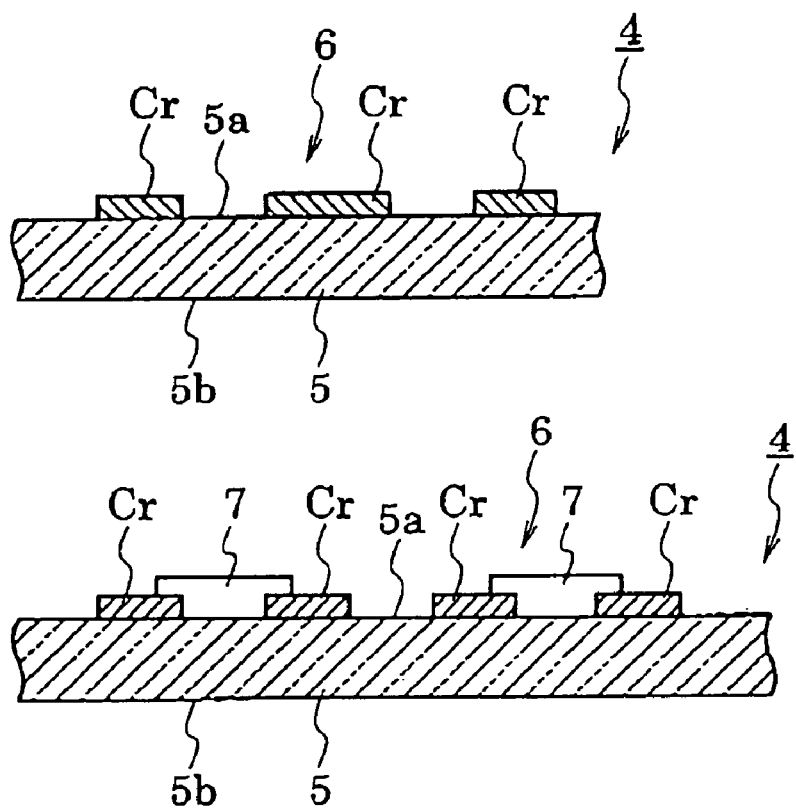

MASK DEFECT INSPECTION APPARATUS

BACKGROUND OF THE INVENTION

1. Field of the Invention

The present invention relates to an improvement in a mask defect inspection apparatus for inspecting a defect in a mask having a pattern (for example, break, thinning or attachment of foreign substance) formed on or in a sample of a photomask or a glass wafer used for fabrication of semiconductors.

2. Description of the Related Art

Heretofore, in a mask defect inspection apparatus for inspecting a defect in a pattern formed on a photomask used for fabrication of semiconductors, there has been known an apparatus in which a chip having a pattern drawn is observed using one detection optical system and an observed image is then compared with a standard image which corresponds to design data to inspect the defect in the mask.

In addition, as the conventional mask defect inspection apparatus of this kind, there has been also known an apparatus in which a reflection-illumination optical system and a transmission-illumination optical system are provided as a detection optical system so that an inspection of defect in the mask may be made with higher sensitivity (for reference, see JP-A 10-97053).

With a development in miniaturization of semiconductor devices, a wavelength of illumination light used for exposure and inspection is increasingly shortened, and deep-ultraviolet rays (DUV) are being used as the illumination light in the mask defect inspection apparatus in the recent years.

On the other hand, since the detection optical system used for the mask defect inspection apparatus has performance equivalent to that of a high-resolution microscope and uses an objective lens of high numerical aperture (high NA), such a detection optical system has high resolving power but shallow depth of focus. As a result, the detection optical system has properties that the depth of focus becomes shallower as the wavelength of illumination light becomes shorter.

Accordingly, the conventional apparatus of this type performs the inspection by finely tuning a focal plane of the detection optical system as well as by switching over an inspection carried out with transmission-illumination light and an inspection carried out with reflection-illumination light, so that it may be identified whether a detected defect is mainly due to the residue of the film-forming material or attachment of the foreign substance onto the mask.

However, while the conventional mask defect inspection apparatus of this type is on a trend that the shortening of wavelength is called for and the depth of focus becomes shallower, there is a tendency that a size in film thickness of the pattern of the mask as an object to be inspected is becoming thicker. Moreover, in addition to a demand for strict accuracy in finely tuning the focal plane for both the inspection using the transmission-illumination and the inspection using the reflection-illumination, there has also been a demand for enlarging a range of tuning of the focal plane. Therefore, the conventional mask inspection apparatus is posing troubles in terms of a prompt inspection and identification of the defect in the mask.

SUMMARY OF THE INVENTION

Therefore, the present invention has been made in view of the above circumstances, and at least one objective of the present invention is to provide a mask defect inspection apparatus capable of carrying out an inspection of defect in a mask simultaneously and easily identifying type of the defect although the wavelength of illumination light becomes shorter and the film-thickness of a pattern of the mask becomes greater.

To achieve these and other advantages and in accordance with the purpose of the invention, as embodied and broadly described herein, the invention provides a mask defect inspection apparatus. The mask defect inspection apparatus comprises an illumination optical system for illuminating a mask on which a pattern is formed; an objective lens facing the mask; at least a pair of detection optical systems each having a detection sensor for obtaining an image of the pattern of the mask, and adapted to receive illumination lights from illumination areas different from each other through the objective lens, respectively; and a focusing changing device for changing a position of focusing between sites of the pattern in a film-thickness direction of the mask and the pattern images obtained by each of the detection sensors, such that pattern images obtained by each of the detection sensors are changed corresponding to the film-thickness direction of the mask.

According to the present invention, since the different areas of the mask formed with the pattern are illuminated and the illumination lights from the different areas are received by the respective detection optical systems so that the pattern images may be obtained simultaneously corresponding to the different areas illuminated, it is possible to simultaneously carry out the inspection of defect for the different areas. In addition, since the focusing position between the pattern sites in the film-thickness direction of the mask and the pattern images obtained by each of the detection sensors is changed such that the pattern images obtained by the detection sensors change corresponding to the film-thickness direction of the mask, it is possible to carry out the identification of the defect in the mask easily even when the mask is thick in the direction of film-thickness of the mask.

To achieve these and other advantages and in accordance with the purpose of the invention, as embodied and broadly described herein, the invention provides a mask defect inspection apparatus. The mask defect inspection apparatus comprises an illumination optical system configured to illuminate a plurality of illumination areas different from each other of a mask on which a pattern is formed; an objective lens facing the mask; at least two detection optical systems each configured to receive illumination light from a corresponding one of the illumination areas different from each other of the mask through the objective lens, and each having a detection sensor configured to obtain an image of the pattern in the corresponding one of the illumination areas of the mask based on the illumination light from the corresponding one of the illumination areas of the mask received by the corresponding one of the at least two detection optical systems; and a focusing changing device configured to change a position of focusing between sites of the pattern in a film-thickness direction of the mask and the pattern image obtained by each of the detection sensors, such that pattern obtained by each of the detection sensors are changed corresponding to the film-thickness direction of the mask.

(1) The focusing changing device decides the focusing position between the pattern sites in the film-thickness direction of the mask and the pattern images obtained by each of the detection sensors according to a cross-sectional structure of the pattern in the film-thickness direction.

According to the embodiment (1) of the present invention, since the focusing position between the pattern sites in the film-thickness direction of the mask and the pattern images obtained by the detection sensors is decided by the focusing changing device according to the cross-sectional structure of the pattern in the film-thickness direction, it is possible to carry out the inspection of the defect promptly.

(2) One of the detection optical systems is a transmission-detection optical system for forming the pattern image of the illumination area illuminated by transmission-illumination light on the detection sensor, and the other of the detection optical systems is a reflection-detection optical system for forming the pattern image of the illumination area illuminated by reflection-illumination light on the detection sensor.

(3) The focusing changing device decides the focusing position between the pattern sites in the film-thickness direction of the mask and the pattern images obtained by each of the detection sensors based on inspection object information of whether to inspect a foreign substance attached on the mask or to inspect a residual substance of a film-forming material forming the pattern.

(4) The focusing changing device comprises a moving mechanism for moving either the mask or the objective lens in a direction of an optical axis of the objective lens.

(5) The focusing changing device comprises a moving mechanism for moving the detection sensor in a direction of an optical axis of the detection optical system while a distance between the mask and the objective lens is maintained constant.

(6) Each of the detection optical systems has a focusing lens, and the focusing changing device comprises a moving mechanism for moving the focusing lens in a direction of an optical axis of the focusing lens.

According to the embodiments (2) to (6) of the present invention, by using the transmission-detection optical system and the reflection-detection optical system appropriately, it is possible to carry out the easy and prompt identification of whether the foreign substance is attached on the mask or the film-forming material for forming the pattern remains on the mask.

(7) At least one of the detection optical systems is provided with a plurality of the detection sensors, and the plurality of detection sensors detect images of the pattern site which are different from each other in a direction of thickness of the mask.

According to the embodiment (7) of the present invention, it is possible to carry out the easy and prompt inspection of which pattern site in the thickness direction of the mask has the defect.

(8) The mask defect inspection apparatus further comprises a signal processor, wherein the signal processor controls the focusing changing device and compares the pattern images obtained by each of the detection sensors with standard images to inspect presence or absence of a defect in the mask.

(9) The mask defect inspection apparatus further comprises a monitor, wherein the signal processor outputs the pattern images obtained by each of the detection sensors to the monitor as image data so that the pattern images are observable on the monitor.

According to the embodiments (8) and (9) of the present invention, it is possible to carry out the inspection of the defect easily and promptly.

Another aspect of the present invention provides mask defect inspection apparatus. That is, this mask defect inspection apparatus comprises an illumination optical system for illuminating a mask on which a pattern is formed; an objective lens facing the mask, at least a pair of detection optical systems each having a detection sensor for obtaining an image of the pattern, and adapted to receive illumination lights from illumination areas different from each other through the objective lens, respectively; and a focus adjuster for adjusting focusing between pattern sites of the mask in the film-thickness direction thereof and pattern images obtained by each of the detection sensors, the focus adjuster is adapted for enabling the detecting sensor to form the pattern images corresponding to the pattern sites of the mask in the film-thickness direction thereof, respectively, so that the obtained pattern images may change corresponding to changes in the pattern sites in the film-thickness direction.

Following are preferred embodiments (a) to (g) of the above mask defect inspection apparatus according to the present invention.

Any combinations thereof are considered to be preferred ones of the above mask defect inspection apparatus unless any contradictions occur.

Another aspect of the present invention provides mask defect inspection apparatus. That is, this mask defect inspection apparatus comprises an illumination optical system configured to illuminate a plurality of illumination areas different from each other of a mask on which a pattern is formed; an objective lens facing the mask; at least two detection optical systems each configured to receive illumination light from a corresponding one of the illumination areas different from each other of the mask through the objective lens, and each having a detection sensor configured to obtain an image of the pattern in the corresponding one of the illumination areas of the mask based on the illumination light from the corresponding one of the illumination areas of the mask received by the corresponding one of the at least two detection optical systems; and a focus adjuster configured to adjust focusing between pattern sites of the mask in the film-thickness direction thereof and the pattern image obtained by each of the detection sensors, the focus adjuster is adapted for enabling each of the detecting sensors to form the pattern image corresponding to the pattern site in the corresponding one of the illumination areas of the mask in the film-thickness direction thereof, so that the obtained pattern images are changed corresponding to changes in the pattern sites in the film-thickness direction.

(b) One of the detection optical systems is a transmission-detection optical system for forming the pattern image of the illumination area illuminated by transmission-illumination light on the detection sensor, and the other of the detection optical systems is a reflection-detection optical system for forming the pattern image of the illumination area illuminated by reflection-illumination light on the detection sensor.

(c) The focus adjuster adjusts the focusing between the pattern sites in the film-thickness direction of the mask and the pattern images obtained by each of the detection sensors based on inspection object information of whether to inspect a foreign substance attached on the mask or to inspect a residual substance of a film-forming material forming the pattern.

(d) The focus adjuster comprises a moving mechanism for moving either the mask or the objective lens in a direction of an optical axis of the objective lens.

(e) The focus adjuster comprises a moving mechanism for moving the detection sensor in a direction of an optical axis of the detection optical system while a distance between the mask and the objective lens is maintained constant.

(f) Each of the detection optical systems has a focusing lens, and the focus adjuster comprises a moving mechanism for moving the focusing lens in a direction of an optical axis of the focusing lens.

(g) At least one of the detection optical systems is provided with a plurality of the detection sensors, and the plurality of detection sensors detect images of the pattern site which are different from each other in a direction of thickness of the mask.

It is to be understood that both the foregoing general description and the following detailed description are exemplary, and are intended to provide further explanation of the invention as claimed.

This application claims priority of Japanese Patent Application No. 2004-81767, filed on Mar. 22, 2004, the entirety of which is incorporated by reference herein.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIGS. 3A to 3C are diagrams to explain types of masks, wherein FIG. 3A shows a state that a predetermined pattern is formed on a surface of a quartz glass with a film-forming material, FIG. 3B shows a state that a pattern is formed on the surface of the quartz glass with the film-forming material and a phase shifter, and FIG. 3C shows a state that a pattern is formed by providing the film-forming material on the surface of the quartz glass and engraving grooves on the surface.

FIGS. 4A to 4C show examples of defects cause on the mask, wherein FIG. 4A shows thinning of the pattern, FIG. 4B shows that the film-forming material remains between the film-forming material and the film-forming material, and FIG. 4C shows a state that a foreign substance is attached on a surface of the film-forming material.

FIGS. 5A to 5C show examples of defects cause on the mask seen from a cross-sectional direction, wherein FIG. 5A shows the foreign substance attached on the surface of the film-forming material, FIG. 5B shows a state that foreign substances are attached on the surfaces of the quartz glass and the phase shifter, and FIG. 5C shows a state that the foreign substance is attached on the groove and a residual substance of the film-forming material exists on the surface of the film-forming material.

DESCRIPTION OF THE PREFERRED EMBODIMENTS

Figure 1:
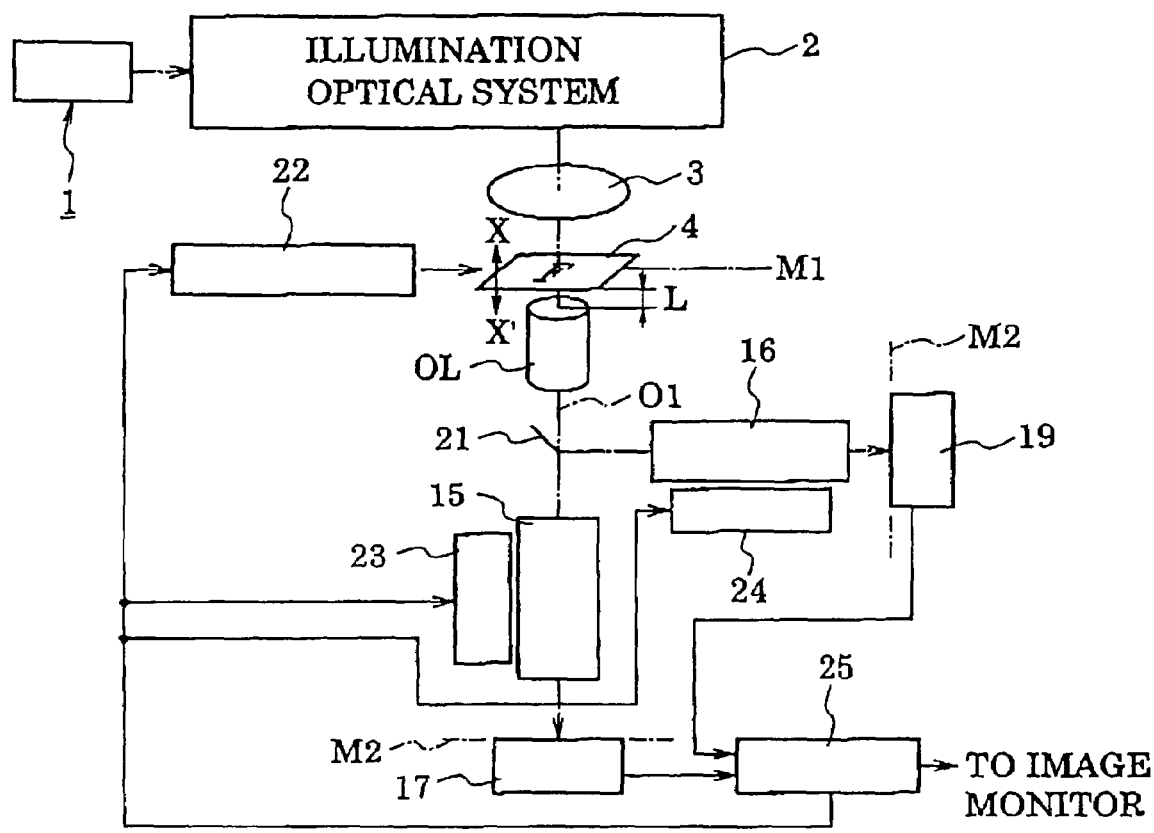
FIG. 1 is a diagram schematically showing an optical system according to a first embodiment of a mask defect inspection apparatus of the present invention.

Reference will now be made in detail to the present preferred embodiments of the invention, examples of which are illustrated in the accompanying drawings. Wherever possible, the same reference numbers are used in the drawings and the description to refer to the same or like parts.

First Embodiment

FIG. 1 shows a first embodiment of a mask defect inspection apparatus according to the present invention, in which reference number 1 denotes an illumination light source, 2 is an illumination optical system, 3 is a condenser lens, 4 is a mask as a sample, and OL represents an objective lens.

Figure 2:
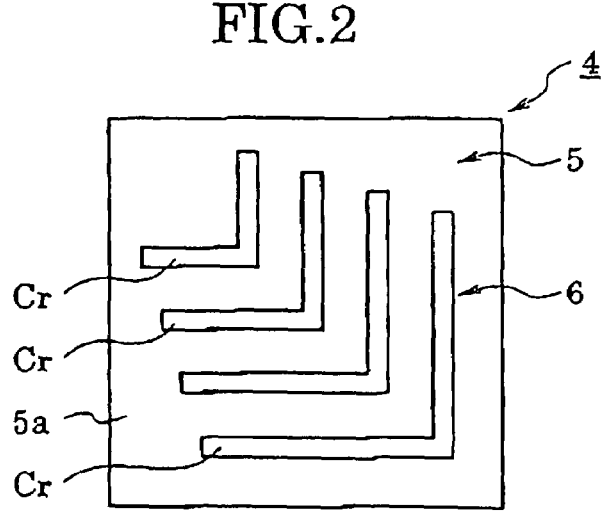
FIG. 2 is a diagram schematically showing one example of a pattern formed on a mask.

As schematically shown in FIG. 2, for example, a pattern 6 is formed on a surface 5a of a quartz glass 5 as a transparent substrate of the mask 4 with Cr (chromium) as a film-forming material. There are various types of cross-sectional structures in a direction of film-thickness of the pattern 6 formed on the mask 4. For example, FIG. 3A shows that the pattern 6 is formed by providing a Cr film as the film-forming material on the surface 5a of the quartz glass 5, FIG. 3B shows that the pattern 6 is formed by providing the Cr film on the surface 5a of the quartz glass 5 at an equal interval and providing a phase shifter material 7 between the Cr film and the Cr film, and FIG. 3C shows that the pattern 6 is formed by providing the Cr film on the surface 5a of the quartz glass 5 at an equal interval and engraving a groove 8 on the surface 5a of the quartz glass 5.

Figure 4A:
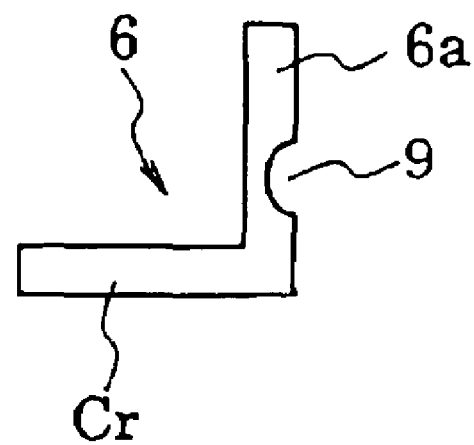
Figure 4B:
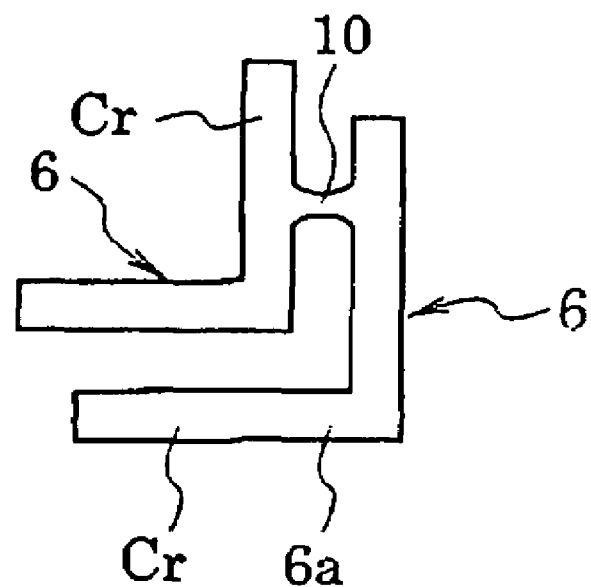
Figure 4C:
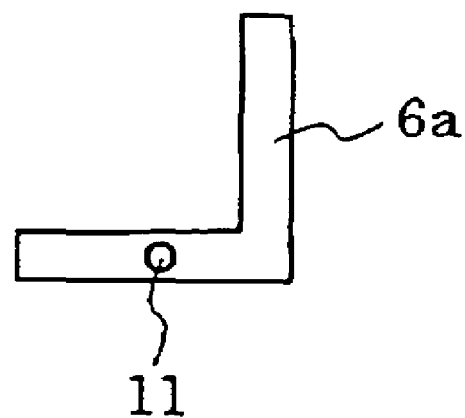

The mask 4 of this kind is formed by vapor depositing the Cr on the surface 5a of the quartz glass 5 and coating a photoresist thereon, exposing a part of the photoresist thereafter and removing the Cr by etching, and so on. However, various defects may exist on the mask 4 if it is seen from the top, such as a pattern-thinning defect 9 as schematically shown in FIG. 4A in which a part of the Cr film forming the pattern 6 is removed and hence the pattern 6 is slenderized, a film-forming material residual defect 10 as shown in FIG. 4B in which the Cr as the film-forming material remains in such a manner as to bridge between the Cr film forming the pattern 6 and another Cr film, and a foreign substance attachment defect 11 as shown in FIG. 4C in which the foreign substance is attached to a surface 6a of the Cr film forming the pattern 6.

Figure 5A:
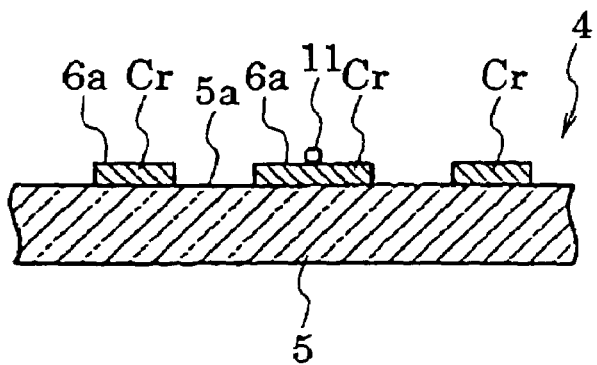
Figure 5B:
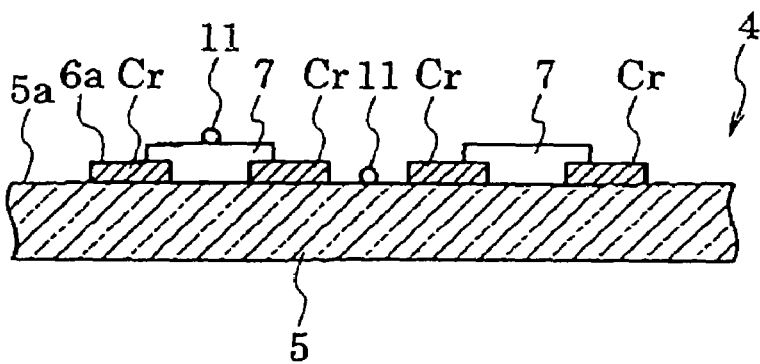
Figure 5C:
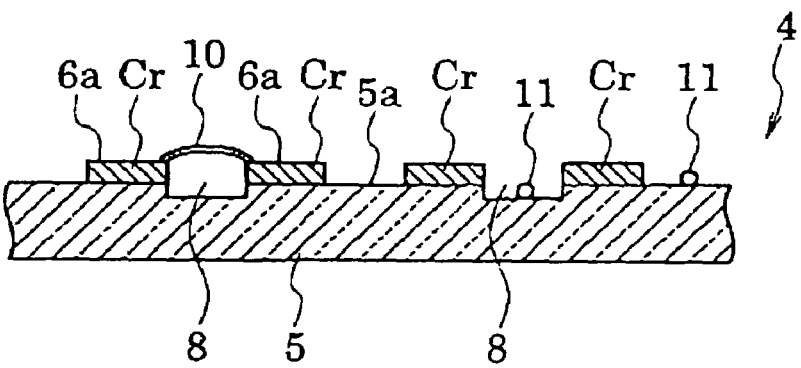

When such defects are seen in a cross-sectional view taken in the film-thickness direction of the pattern 6, for example, the foreign substance attachment defect 11 may exist on the surface 6a of the Cr film as shown in FIG. 5A or exist on a surface of the phase shifter material 7 or on the surface 5a of the quartz glass 5 as shown in FIG. 5B. As shown in FIG. 5C, the film-forming material residual defect 10 may exist in such a manner as to bridge between the surface 6a of one Cr film and the surface 6a of another Cr film instead of existing on the surface 5a of the quartz glass 5.

For example, a laser is used for the illumination light source 1. The illumination optical system 2 is provided with a laser coherence reduction mechanism and an integrator. Since a structure of the illumination optical system 2 is disclosed in JP-A 2002-39960 and in Japanese patent application No. 2003-209043 for example, its explanation will not be given in detail.

Figure 6:
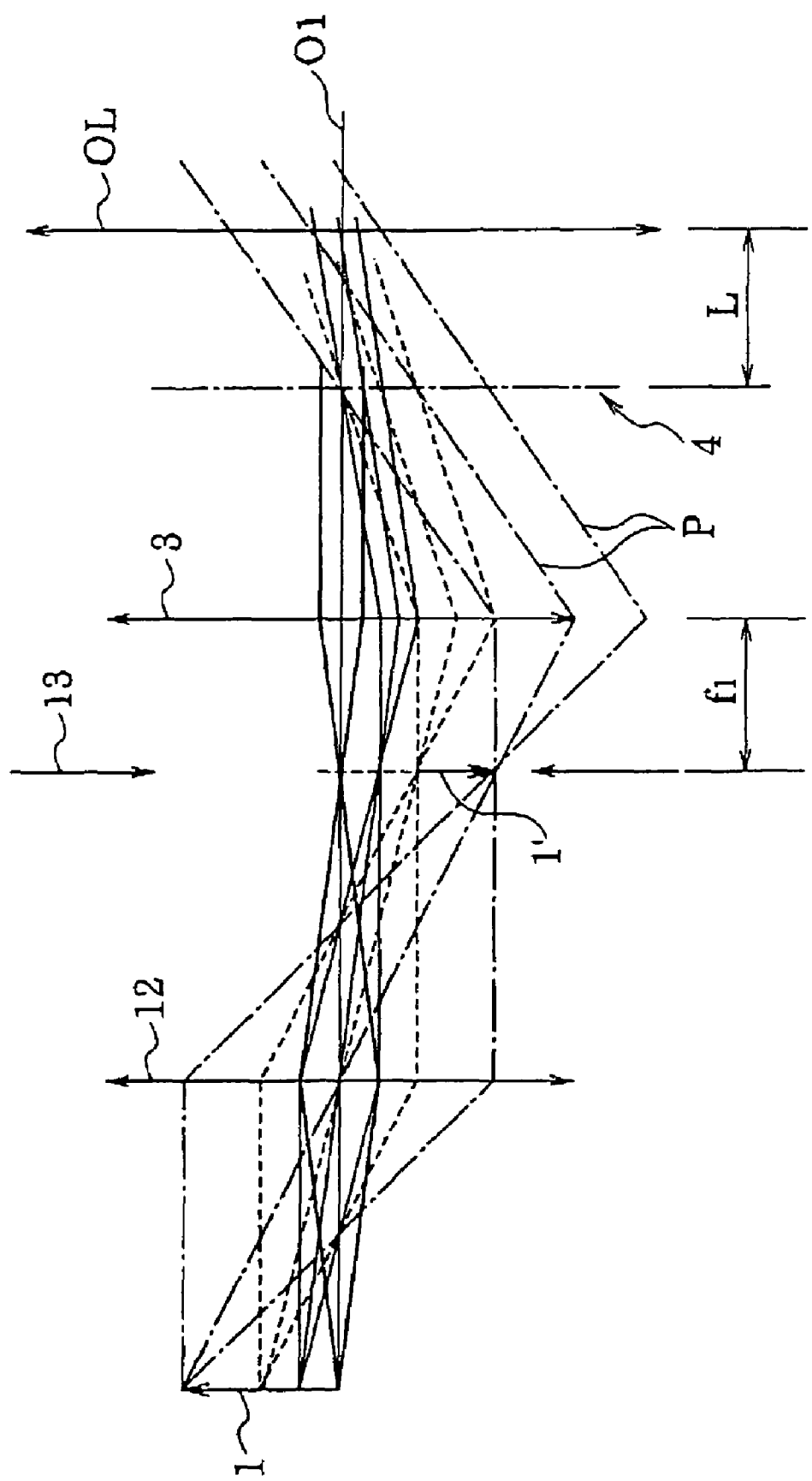
FIG. 6 is an optical diagram for explaining general conception of an illumination optical system according to a Kohler illumination method.

The mask 4 is illuminated for example by a well-known Kohler illumination method using the condenser lens 3. As schematically shown in FIG. 6, the illumination light source 1 is once imaged on a front focal plane f1 of the condenser lens 3 as a light source image 1' by a light-focusing lens 12, and illumination light which exits from the front focal plane f1 illuminates the mask 4 as a parallel light flux P. Reference number 13 in FIG. 6 denotes an aperture stop.

Figure 7:
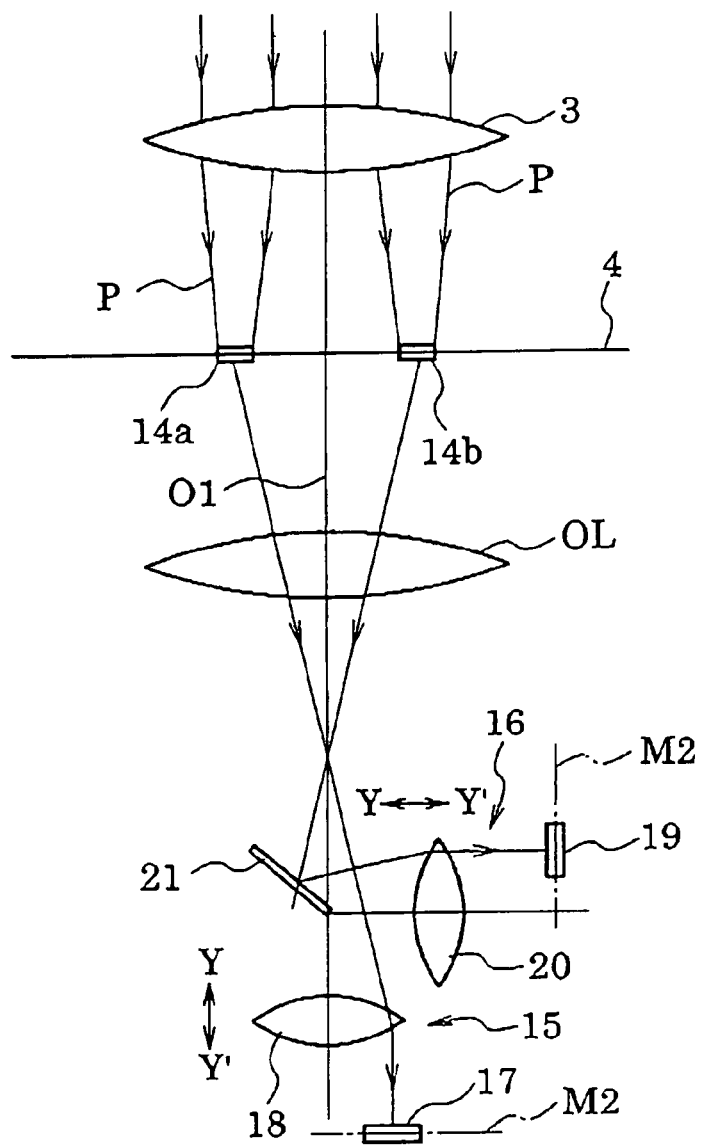
FIG. 7 is a diagram schematically showing different areas of the mask illuminated by the illumination optical system shown in FIG. 1 and a disposition relationship between detection optical systems and those areas.
Figure 8:
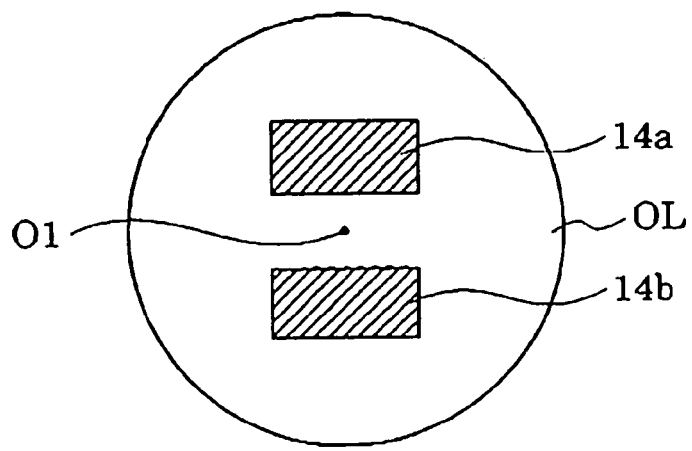
FIG. 8 is a plan view showing a positional relationship of the areas and an objective lens shown in FIG. 7.

As schematically shown in FIG. 7, the illumination optical system 2 illuminates different areas 14a and 14b of the mask 4. The objective lens OL faces the mark 4. Detection optical systems 15 and 16 also face the mask 4 through the objective lens OL. As schematically shown in FIG. 7, the detection optical system 15 has a focusing lens 18 which receives transmission-illumination light from the area 14a obtained through the objective lens OL and forms a pattern image based on the area 14a on a detection sensor 17. The detection optical system 16 has a focusing lens 20 which receives transmission-illumination light from the area 14b obtained through the objective lens OL and forms a pattern image of the area 14b on a detection sensor 19. As schematically shown in FIG. 8, when a positional relationship of the areas 14a and 14b is seen from the top in perpendicular to an optical axis O1 of the objective lens OL, the area 14a and the area 14b are provided at positions symmetrical in such a manner that the optical axis O1 is interposed between the areas 14a and 14b. Reference numeral 21 denoted in FIG. 7 is a total reflection mirror for reflecting the illumination light from the area 14b toward the focusing lens 20.

The mask 4 is configured to be movable in a direction of optical axis (in a direction of arrows X-X') of the objective lens OL by a mask position control mechanism (moving mechanism) 22 shown in FIG. 1, thereby a distance L from the surface 5a of the quartz glass 5 of the mask 4 to the center of the objective lens OL can be adjustable.

Figure 9:
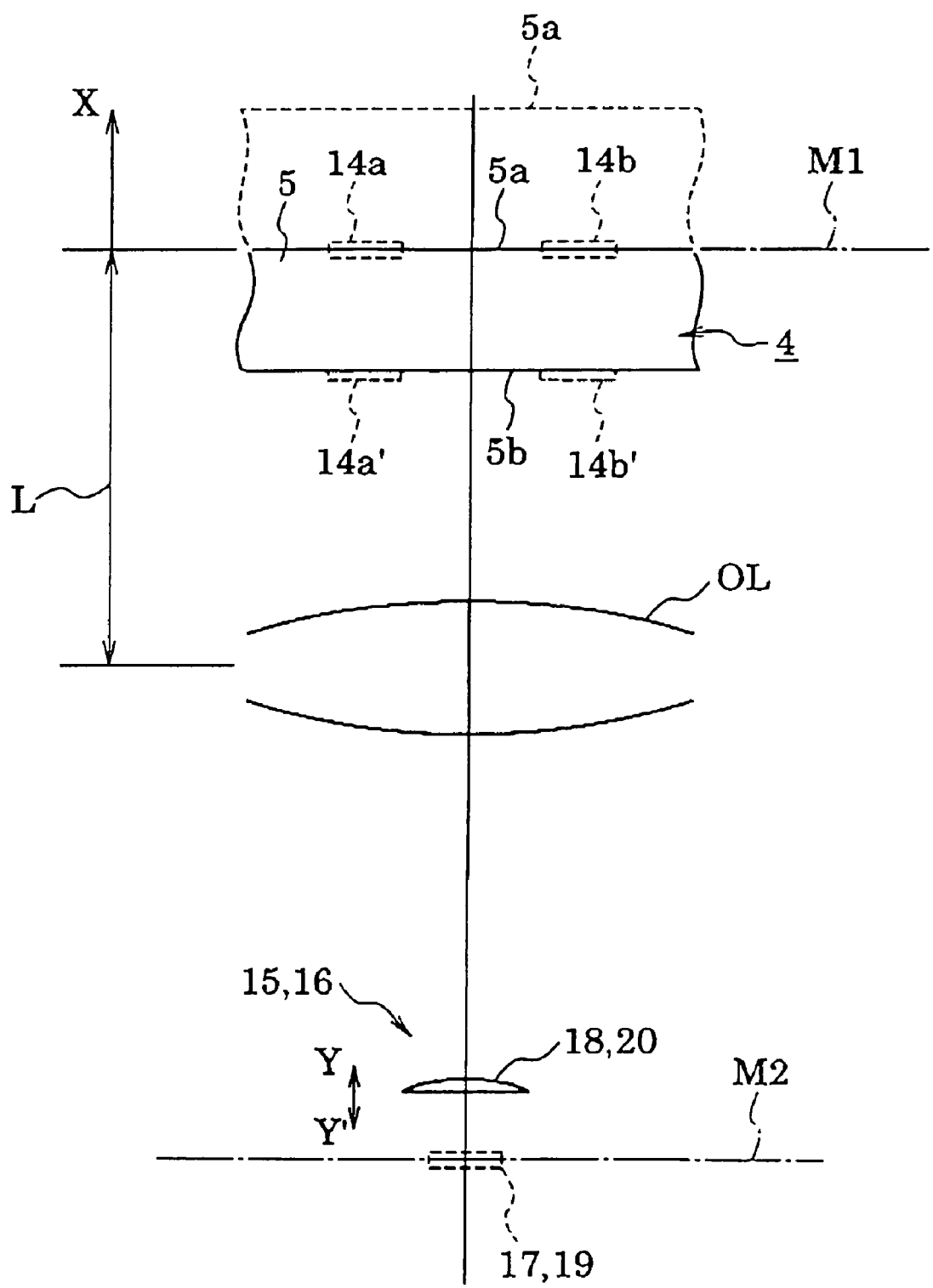
FIG. 9 is a diagram showing pattern sites in a direction of film-thickness of the mask and a relationship between an object surface and an image surface on a conceptual basis.

A conjugate relationship between an object surface M1 and an image surface M2 relative to the objective lens OL is defined by optical performance of the objective lens OL. As schematically shown in FIG. 9, given that the areas 14a and 14b of the surface 5a of the quartz glass 5 are on the object surface M1 and the detection sensors 17 and 19 are on the image surface M2, pattern images corresponding to pattern sites existing at the areas 14a and 14b of the surface 5a of the quartz glass 5 are formed on the detection sensors 17 and 19.

At this point, when the mask 4 is moved in the direction X along the optical axis O1 to locate a back surface 5b of the quartz glass 5 at the object surface M1, pattern images corresponding to pattern sites existing at areas 14a' and 14b' of the back surface 5b of the quartz glass 6 are formed on the detection sensors 17 and 19.

More specifically, when the distance L between the mask 4 and the objective lens OL is changed by the mask position control mechanism 22, a position of the object surface M1 in the film-thickness direction with respect to the mask 4 is changed relatively. As a result, the pattern images of the pattern sites obtained by the detection sensors 17 and 19 are changed in the film-thickness direction. Therefore, the mask position control mechanism 22 functions as focusing changing means (focusing changing device, focus adjuster) for changing a position (relation) of focusing between the pattern sites in the film-thickness direction of the mask 4 and the pattern images obtained by the detection sensors 17 and 19, such that the pattern images obtained by the detection sensors 17 and 19 may change corresponding to the film-thickness direction of the mask 4.

The detection optical system 15 is provided with a focusing control mechanism (moving mechanism) 23, and the detection optical system 16 is provided with a focusing control mechanism (moving mechanism) 24. The focusing control mechanism 23 has a function to control the focusing lens 18 in the direction of an optical axis of the focusing lens 18 (in the direction of Y-Y'), and the focusing control mechanism 24 similarly has a function to control the focusing lens 20 in the direction of an optical axis of the focusing lens 20 (in the direction of Y-Y'). When the distance L between the mask 4 and the objective lens OL is maintained constant and the focusing lenses 18 and 20 are adjusted in the optical axis directions, focusing positions of the pattern images relative to image surfaces M2 and M2 are changed by the focusing lenses 18 and 20, and thereby, fine-tuning of focuses of the pattern images formed on the detection sensors 17 and 19 are carried out. Therefore, the focusing control mechanism 23 and 24 also function as focusing changing means (focusing changing device, focus adjuster) for changing the focusing position between the pattern sites in the film-thickness direction of the mask 4 and the pattern images obtained by the detection sensors 17 and 19 so that the pattern images obtained by the detection sensors 17 and 19 may change corresponding to the film-thickness direction of the mask 4.

The mask position control mechanism 22, and focusing control mechanisms 23 and 24 are controlled by a signal processing system (signal processor) 26. The signal processing system 25 compares the pattern images obtained by the detection sensors 17 and 19 with a standard image which is planed in terms of design, to inspect the presence or absence of defect in the mask 4.

In addition, the signal processing system 25 outputs the pattern images obtained by the detection sensors 17 and 19 to an image monitor (not illustrated) as image data. Accordingly, in the mask defect inspection apparatus, it is possible to observe the pattern images on a screen of the image monitor.

Identification of type of defect is for example, carried out by comparing and considering a defect according to a pattern image obtained at the time when the surface 5a of the quartz glass 5 is in focus and a defect according to a pattern image obtained at the time when the surface of the film-forming material is in focus.

There are various types of cross-sectional structures of the pattern 6 in the direction of film-thickness as shown in FIGS. 3A to 3C for example. Therefore, if data corresponding to the cross-sectional structures are previously stored in the signal processing system 25 and a distance of the mask 4 relative to the objective lens OL is decided on the basis of a cross-sectional structure of the mask 4 to be inspected, it is possible to carry out the inspection of defect promptly.

Also, the focusing position between the pattern sites in the film-thickness direction of the mask 4 and the pattern images obtained by the detection sensors 17 and 19 may be decided by the distance of the mask 4 relative to the objective lens OL, based on inspection object information of whether to inspect the foreign substance attached on the mask 4 or to inspect a residual substance of the film-forming material forming the pattern.

Although the illumination optical system 2 is configured to illuminate the different areas 14a and 14b of the mask 4 separately in the first embodiment, it is to be noted that this configuration is for convenience of explanation. As a matter of course, the illumination optical system may be configured to illuminate a wide area including the areas 14a and 14b.

Second Embodiment

Figure 10:
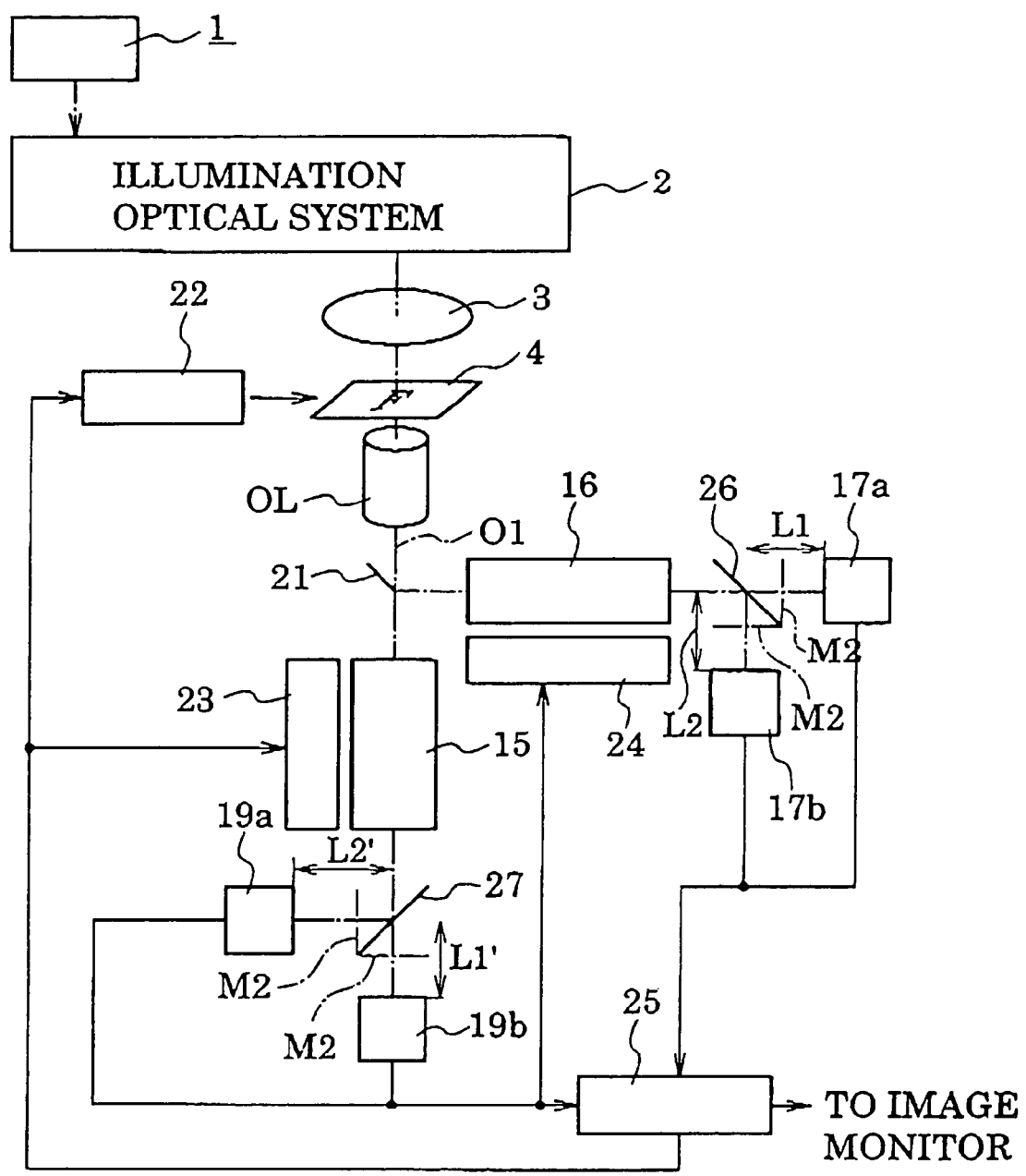
FIG. 10 is a diagram schematically showing an optical system according to a second embodiment of the mask defect inspection apparatus of the present invention.

FIG. 10 is a diagram schematically showing a second embodiment of the mask defect inspection apparatus according to the present invention. In the mask defect inspection apparatus of the second embodiment, the detection optical systems 15 and 16 are provided with half mirrors 26 and 27, respectively, for dividing the illumination light obtained through the focusing lenses 18 and 20 into two. Toward the directions reflected by the half mirrors 26 and 27, there are provided detection sensors 17a, 17b, 19a and 19b, respectively.

It is to be noted that a distance L1 from the detection sensor 17a to the half mirror 26 and a distance L2 from the detection sensor 17b to the half mirror 26 are different from each other. Likewise, a distance L1' from the detection sensor 19a to the half mirror 27 and a distance L2' from the detection sensor 19b to the half mirror 27 are different from each other as well. In other words, the distances of the detection sensor 17a (19a) and the detection sensor 17b (19b) relative to the image surfaces M2 are different. Accordingly, when such a structure is employed in which at least one of the detection optical systems is provided with a plurality of detection sensors and the distances of the detection sensors relative to the image surfaces M2 are differentiated from each other, each focal plane becomes different with regard to each of the detection sensors 17a (19a) and 17b (19b). As a result, a pattern image obtained by the detection sensor 17a (19a) and a pattern image obtained by the detection sensor 17b (19b) become images of a pattern site which are different from each other in a direction of thickness of the mask 4. Hence, it is possible to identify promptly which of positions of the pattern site in the thickness direction of the mask 4 has the defect.

For example, as shown in FIG. 5C, it is possible to inspect whether the foreign substance attachment defect 11 exists on the surface 5a or on the groove 8 of the quartz glass 5, promptly, according to the second embodiment of the present invention.

Third Embodiment

Figure 11:
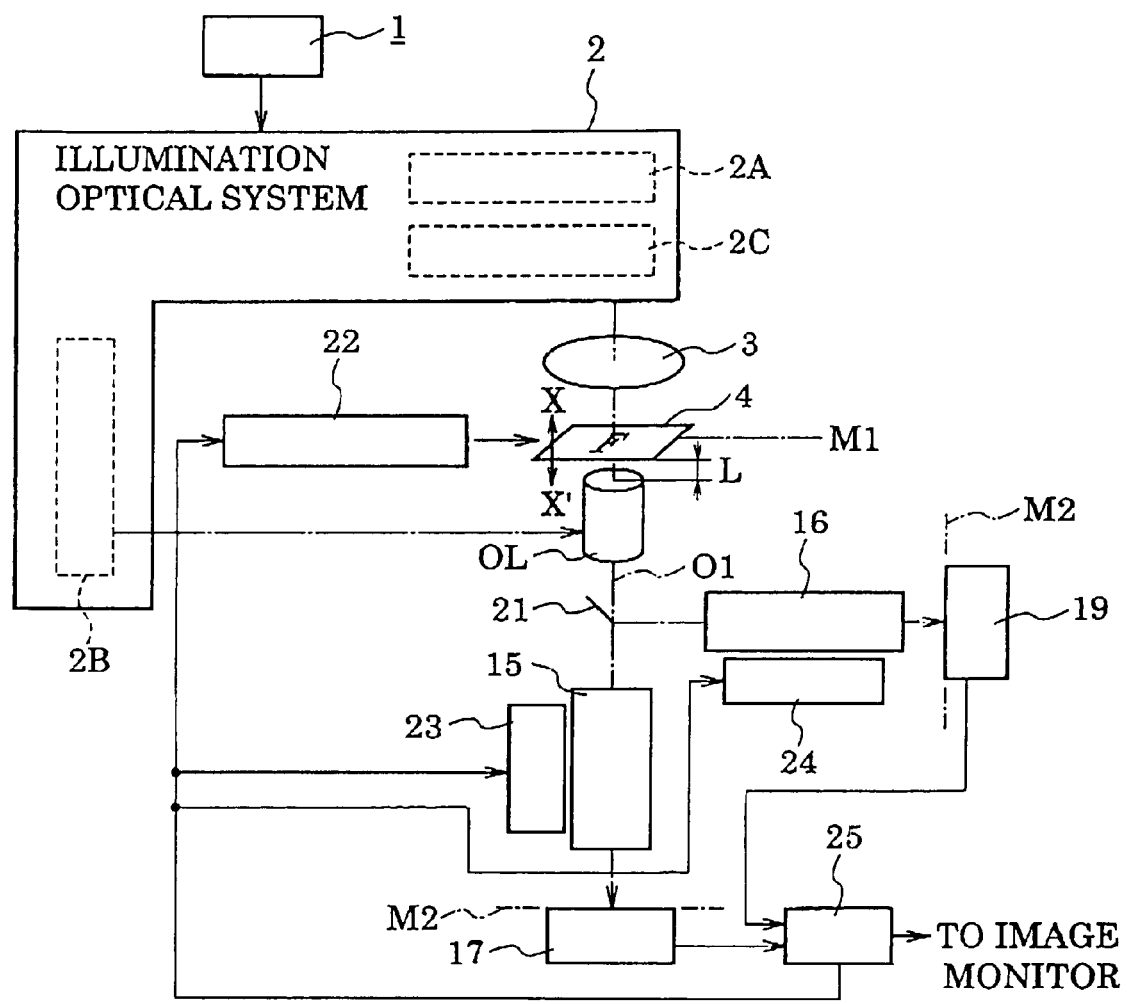
FIG. 11 is a diagram schematically showing an optical system according to a third embodiment of the mask defect inspection apparatus of the present invention.

FIG. 11 is a diagram schematically showing a third embodiment of the mask defect inspection apparatus according to the present invention. In the mask defect inspection apparatus of the third embodiment, the illumination optical system 2 is provided with a transmission-type illumination optical system 2A for illuminating the mask 4 from the surface 5a of the quartz glass 5 of the mask 4 and a reflection-type illumination optical system 2B for illuminating the mask 4 from the back surface 5b of the quartz glass 5 of the mask 4. In this embodiment, the transmission-type illumination optical system 2A is provided with an illumination light switch-over mechanism 2C for carrying out switching over of the illumination light between the transmission-illumination light and the reflection-illumination light. However, the skilled artisan will readily recognize that the reflection-type illumination optical system 2B may be provided with such an illumination light switch-over mechanism 2C instead of providing the optical system 2A with the mechanism 2C.

Figure 12:
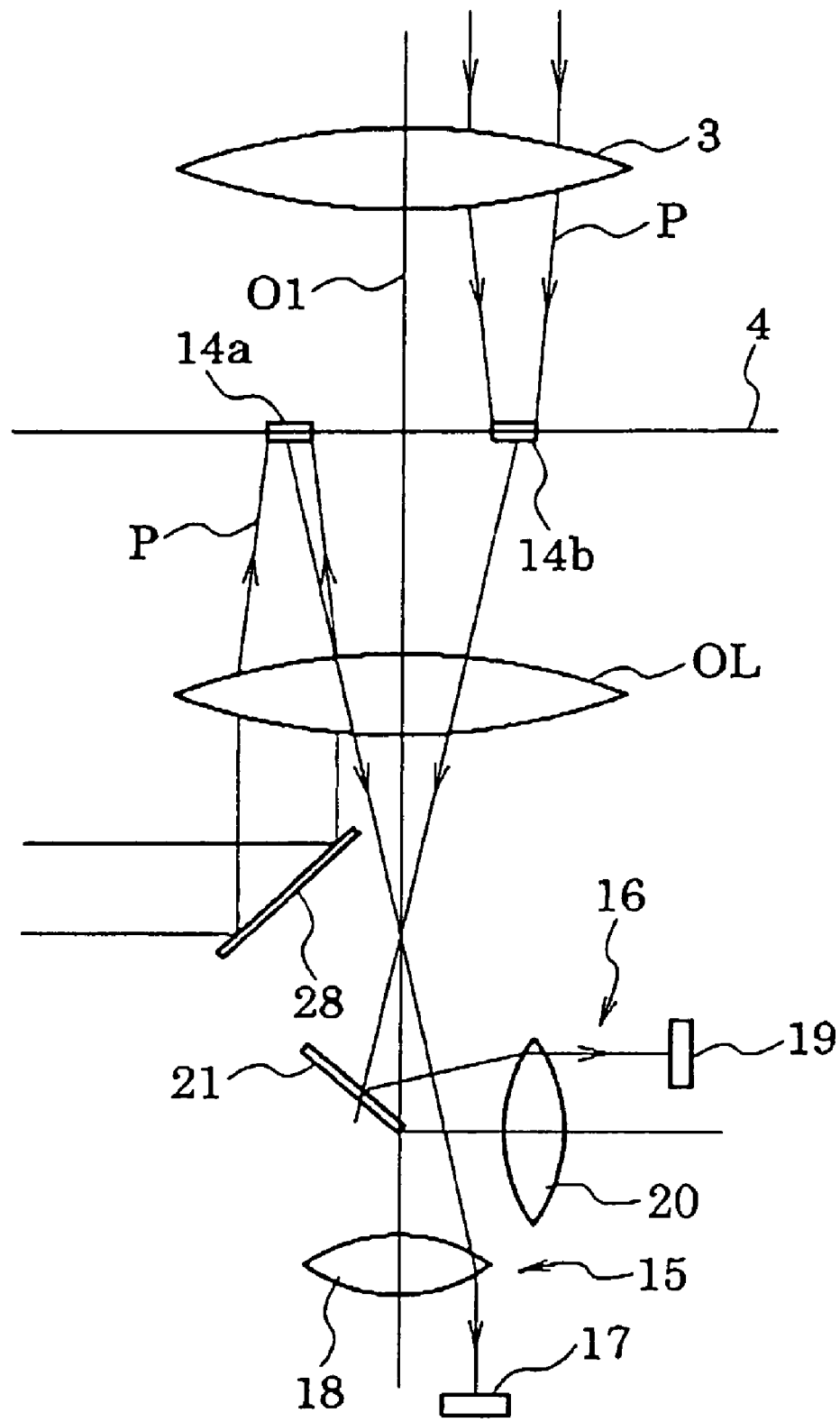
FIG. 12 is a diagram schematically showing a relationship between detection optical systems and illumination areas shown in FIG. 11.

As shown in FIG. 12, the reflection-type illumination optical system 2B is provided with a light-focusing lens which is not illustrated and a reflection mirror 28 for reflecting the illumination light toward the objective lens OL. The reflection-type illumination optical system 2B illuminates the mask 4 for example by the Kohler illumination method. The light focusing lens forms a light source image of the light source 1 on a focal plane of the objective lens OL. The objective lens OL converts its illumination light into a parallel light flux to illuminate the area 14a as the reflection-illumination light.

The detection optical system 15 is disposed to face the area 14a through the objective lens OL, and the detection optical system 16 is disposed to face the area 14b through the objective lens OL. The detection optical system 15 functions as a reflection-detection optical system for forming a pattern image of the area 14a illuminated by the reflection-illumination light on the detection sensor 17, and the detection optical system 16 functions as a transmission-detection optical system for forming a pattern image of the area 14b illuminated by the transmission-illumination light on the detection sensor 19.

It is not easy to differentiate images when a same area is illuminated simultaneously by the transmission-type illumination and the reflection-type illumination and the pattern images are retrieved by same detection optical system, since the pattern images overlap with each other. However, when the detection optical systems 15 and 16 are differentiated into and used as the transmission-detection optical system and the reflection-detection optical system, and at the same time, when the different areas 14a and 14b are illuminated simultaneously as in the present embodiment, it is possible to retrieve the pattern images simultaneously without causing the pattern images to be overlapped. Therefore, it is possible to promptly carry out the identification of whether the foreign substance is attached on the mask 4 or the film-forming material for forming the pattern remains on the mask 4.

As well as in this embodiment, the focusing position between the pattern sites in the film-thickness direction of the mask 4 and the pattern images obtained by the detection sensors 17 and 19 may be decided by the distance L of the mask 4 relative to the objective lens OL, based on the inspection object information of whether to inspect the foreign substance attached on the mask 4 or to inspect the residual substance of the film-forming material forming the pattern.

More specifically, if a position of the surface 5a of the quartz glass 6 and a position of the surface 6a of the film-forming material are calculated by calibration carried out before the inspection and positions in focus of the detection sensors 17 and 19 are previously set on the basis of whether the object to be inspected is the residual substance of the film-forming material attached on the mask 4 or the foreign substance attached on the mask 4, it is possible to ensure the prompt inspection of the defect.

In addition, if the illumination optical system 2A is switched-over from the illumination type of transmission-illumination to the illumination type of reflection-illumination by using the illumination light switch-over mechanism 2C, it is possible to retrieve the pattern image according to the transmission-illumination and the pattern image according to the reflection-illumination with the same detection optical system 16 with regard to the same area 14b. Hence, by comparing those pattern images, it is possible to carry out the identification of the defect more easily.

Because a well-known structure can be utilized to the illumination light switch-over mechanism 2C, explanation for its structure will not be given in detail.

Fourth Embodiment

Figure 13:
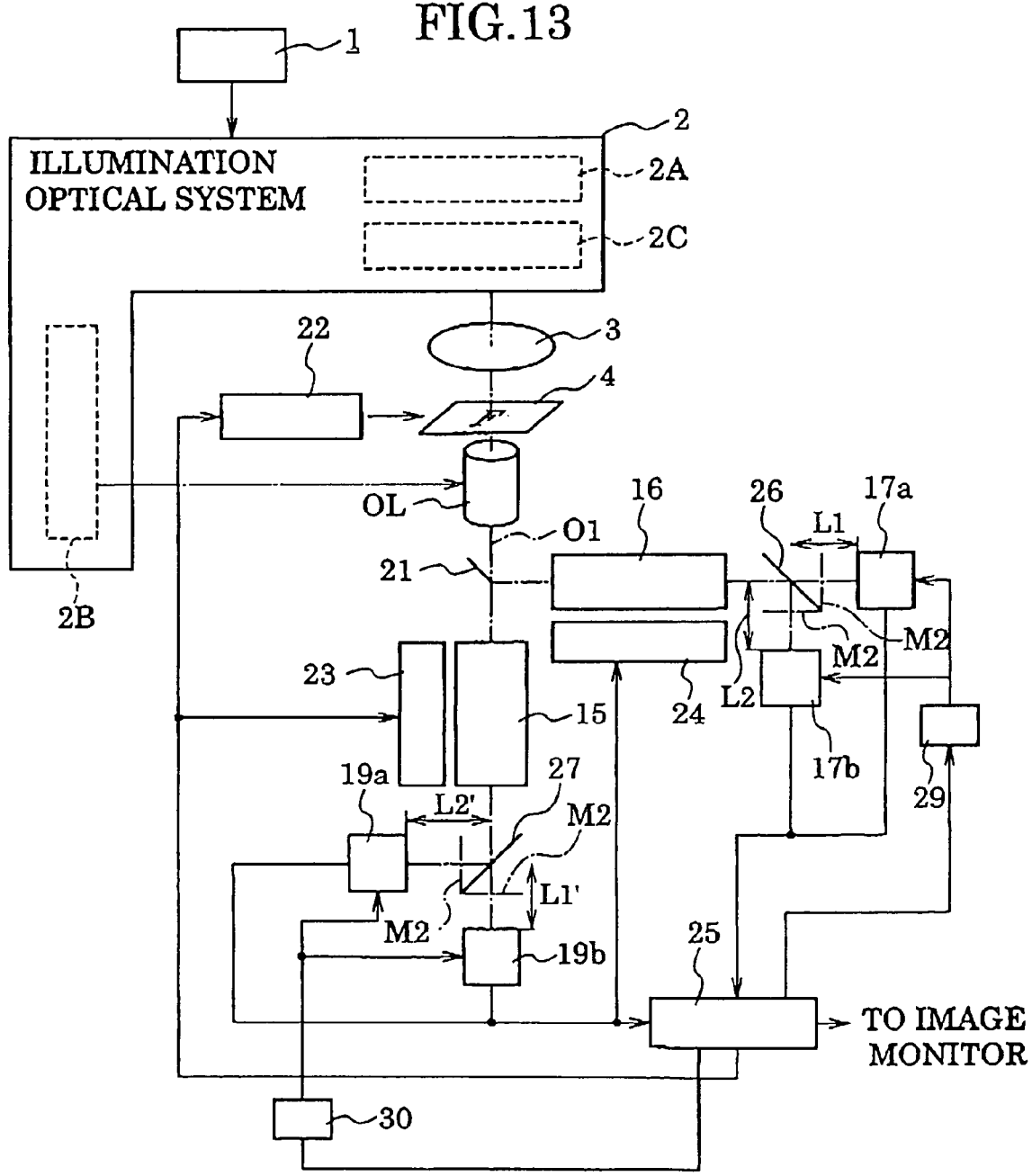
FIG. 13 is a diagram schematically showing an optical system according to a fourth embodiment of the mask defect inspection apparatus of the present invention.

FIG. 13 is a diagram schematically showing a fourth embodiment of the mask defect inspection apparatus according to the present invention. As similar to the second embodiment, in the mask defect inspection apparatus of the fourth embodiment, the detection optical systems 15 and 16 are provided with the half mirrors 26 and 27, respectively, for dividing the illumination light obtained through the focusing lenses 18 and 20 into two. Toward the directions reflected by the half mirrors 26 and 27, there are provided the detection sensors 17a, 17b, 19a and 19b, respectively. The distance L1 from the detection sensor 17a to the half mirror 26 and the distance L2 from the detection sensor 17b to the half mirror 26 are different from each other. Likewise, the distance L1' from the detection sensor 19a to the half mirror 27 and the distance L2' from the detection sensor 19b to the half mirror 27 are also different from each other.

In the fourth embodiment, the detection sensors 17a and 17b are configured to be movable in the optical axis direction of the detection optical system 16 by a sensor moving mechanism (moving mechanism) 29, and the detection sensors 19a and 19b are configured to be movable in the optical axis direction of the detection optical system 15 by a sensor moving mechanism (moving mechanism) 30.

According to this embodiment, when the detection sensors 17a, 17b, 19a and 19b are moved in the optical axis directions in a state that the distance L between the mask 4 and the objective lens OL is held constant and positional relationships of the focusing lenses 18 and 20 relative to the objective lens OL are held constant, focusing positions of pattern images relative to the image surfaces M2 are changed by the detection sensors 17a, 17b, 19a and 19b, thereby finc-tuning for focuses of the pattern images formed on the detection sensors 17a, 17b, 19a and 19b is carried out.

Therefore, in the fourth embodiment, the sensor moving mechanisms 29 and 30 function as focusing changing means (focusing changing device, focus adjuster) for changing the position of focusing between the pattern sites in the film-thickness direction of the mask 4 and the pattern images obtained by the detection sensors 17a, 17b, 19a and 19b so that the pattern images obtained by the detection sensors 17a, 17b, 19a and 19b may change corresponding to the film-thickness direction of the mask 4.

As described in the foregoing, in some of the embodiments of the present invention, the focusing changing means (focusing changing device, focus adjuster) is structured by the mask position control mechanism (mask moving mechanism) 22 which changes the distance L between the objective lens OL and the mask 4 by moving the mask 4 relative to the objective lens OL in the direction of optical axis of the objective lens OL. However, in one embodiment, the focusing changing means (focusing changing device focus adjuster) may be structured by an objective lens moving mechanism (moving mechanism) for moving the objective lens OL in the optical axis direction.

It will be apparent to those skilled in the art that various modifications and variations can be made to the structure of the present invention without departing from the scope or spirit of the invention. In view of the foregoing, it is intended that the present invention covers modifications and variations of this invention provided they fall within the scope of the following claims and their equivalents.

What is claimed is:

1. A mask defect inspection apparatus, comprising:
   an illumination optical system which illuminates a plurality of illumination areas including at least a first illumination area and a second illumination area different from each other of a mask on which a pattern is formed;
   an objective lens facing the mask;
   a first focusing lens which receives first illumination light from the first illumination area of the mask obtained through the objective lens;
   a second focusing lens which receives second illumination light from the second illumination area of the mask obtained through the objective lens;
   a first detection sensor which obtains an image of the pattern in the first illumination area of the mask based on the first illumination light received by the first focusing lens;
   a second detection sensor which obtains an image of the pattern in the second illumination area of the mask based on the second illumination light received by the second focusing lens;
   a first moving mechanism which moves the first detection sensor in a direction of an optical axis of the first detection sensor to change a position of focusing between sites of the pattern in the first illumination area in a film-thickness direction of the mask and the image of the pattern obtained by the first detection sensor, such that the image of the pattern obtained by the first detection sensor is changed corresponding to the film-thickness direction of the mask; and
   a second moving mechanism which moves the second detection sensor in a direction of an optical axis of the second detection sensor to change a position of focusing between sites of the pattern in the second illumination area in the film-thickness direction of the mask and the image of the pattern obtained by the second detection sensor, such that the image of the pattern obtained by the second detection sensor is changed corresponding to the film-thickness direction of the mask.

2. A mask defect inspection apparatus according to claim 1, further comprising a signal processor connected with the first moving mechanism and the second moving mechanism and which controls the first moving mechanism and the second moving mechanism to move the first detection sensor and the second detection sensor.

3. A mask defect inspection apparatus according to claim 2, wherein the signal processor compares the image of the pattern obtained by the first detection sensor and the image of the pattern obtained by the second detection sensor with preset standard images to inspect presence of a defect of the mask.

4. A mask defect inspection apparatus according to claim 3, further comprising a display, wherein the signal processor displays the image of the pattern obtained by the first detection sensor and the image of the pattern obtained by the second detection sensor on the display.

5. A mask defect inspection apparatus according to claim 1, further comprising a third moving mechanism which moves the mask in a direction of an optical axis of the objective lens to change the position of focusing between the sites of the pattern in the first illumination area and the second illumination area in the film-thickness direction of the mask and the images of the pattern obtained by the first detection sensor and the second detection sensor, such that the images of the pattern obtained by the first detection sensor and the second detection sensor are changed corresponding to the film-thickness direction of the mask.

6. A mask defect inspection apparatus according to claim 1, further comprising a fourth moving mechanism which moves the objective lens in a direction of an optical axis of the objective lens to change the position of focusing between the sites of the pattern in the first illumination area and the second illumination area in the film-thickness direction of the mask and the images of the pattern obtained by the first detection sensor and the second detection sensor, such that the images of the pattern obtained by the first detection sensor and the second detection sensor are changed corresponding to the film-thickness direction of the mask.

7. A mask defect inspection apparatus according to claim 1, further comprising:
   a condenser lens provided between the illumination optical system and the mask; and
   a total reflection mirror provided between the objective lens and the first and the second focusing lenses, and which reflects one of the first illumination light from the first illumination area and the second illumination light from the second illumination area of the mask through the objective lens toward one of the first focusing lens and the second focusing lens.

8. A mask defect inspection apparatus, comprising:
an illumination optical system which illuminates a plurality of illumination areas including at least a first illumination area and a second illumination area different from each other of a mask on which a pattern is formed;
an objective lens facing the mask;
a first focusing lens which receives first illumination light from the first illumination area of the mask obtained through the objective lens;
a second focusing lens which receives second illumination light from the second illumination area of the mask obtained through the objective lens;
a first detection sensor which obtains an image of the pattern in the first illumination area of the mask based on the first illumination light received by the first focusing lens;
a second detection sensor which obtains an image of the pattern in the second illumination area of the mask based on the second illumination light received by the second focusing lens;
a first moving mechanism which moves the first focusing lens in a direction of an optical axis of the first focusing lens to change a position of focusing between sites of the pattern in the first illumination area in a film-thickness direction of the mask and the image of the pattern obtained by the first detection sensor, such that the image of the pattern obtained by the first detection sensor is changed corresponding to the film-thickness direction of the mask; and
a second moving mechanism which moves the second focusing lens in a direction of an optical axis of the second focusing lens to change a position of focusing between sites of the pattern in the second illumination area in the film-thickness direction of the mask and the image of the pattern obtained by the second detection sensor, such that the image of the pattern obtained by the second detection sensor is changed corresponding to the film-thickness direction of the mask.

9. A mask defect inspection apparatus according to claim 8, further comprising a signal processor connected with the first moving mechanism and the second moving mechanism and which controls the first moving mechanism and the second moving mechanism to move the first focusing lens and the second focusing lens.

10. A mask defect inspection apparatus according to claim 9, wherein the signal processor compares the image of the pattern obtained by the first detection sensor and the image of the pattern obtained by the second detection sensor with preset standard images to inspect presence of a defect of the mask.

11. A mask defect inspection apparatus according to claim 10, further comprising a display, wherein the signal processor displays the image of the pattern obtained by the first detection sensor and the image of the pattern obtained by the second detection sensor on the display.

12. A mask defect inspection apparatus according to claim 8, further comprising a third moving mechanism which moves the mask in a direction of an optical axis of the objective lens to change the position of focusing between the sites of the pattern in the first illumination area and the second illumination area in the film-thickness direction of the mask and the images of the pattern obtained by the first detection sensor and the second detection sensor, such that the images of the pattern obtained by the first detection sensor and the second detection sensor are changed corresponding to the film-thickness direction of the mask.

13. A mask defect inspection apparatus according to claim 8, further comprising a fourth moving mechanism which moves the objective lens in a direction of an optical axis of the objective lens to change the position of focusing between the sites of the pattern in the first illumination area and the second illumination area in the film-thickness direction of the mask and the images of the pattern obtained by the first detection sensor and the second detection sensor, such that the images of the pattern obtained by the first detection sensor and the second detection sensor are changed corresponding to the film-thickness direction of the mask.

14. A mask defect inspection apparatus according to claim 8, further comprising:
a condenser lens provided between the illumination optical system and the mask; and
a total reflection mirror provided between the objective lens and the first and the second focusing lenses, and which reflects one of the first illumination light from the first illumination area and the second illumination light from the second illumination area of the mask through the objective lens toward one of the first focusing lens and the second focusing lens.

15. A mask defect inspection apparatus comprising:
an illumination optical system which illuminates a plurality of illumination areas including at least a first illumination area and a second illumination area different from each other of a mask on which a pattern is formed;
an objective lens facing the mask;
a first focusing lens which receives first illumination light from the first illumination area of the mask obtained through the objective lens;
a second focusing lens which receives second illumination light from the second illumination area of the mask obtained through the objective lens;
a first detection sensor which obtains an image of the pattern in the first illumination area of the mask based on the first illumination light received by the first focusing lens;
a second detection sensor which obtains an image of the pattern in the second illumination area of the mask based on the second illumination light received by the second focusing lens;
a third detection sensor which obtains the image of the pattern in the first illumination area of the mask based on the first illumination light received by the first focusing lens;
a fourth detection sensor which obtains the image of the pattern in the second illumination area of the mask based on the second illumination light received by the second focusing lens;
a first half-mirror which divides the first illumination light obtained through the first focusing lens into the first illumination light that travels toward the first detection sensor and the first illumination light that travels toward the third detection sensor;
a second half-mirror which divides the second illumination light obtained through the second focusing lens into the second illumination light that travels toward the second detection sensor and the second illumination light that travels toward the fourth detection sensor;
a first moving mechanism which moves the first focusing lens in a direction of an optical axis of the first focusing lens to change a position of focusing between sites of the pattern in the first illumination area in a film-thickness direction of the mask and the images of the pattern obtained by the first detection sensor and the third detection sensor, such that the images of the pattern obtained by the first detection sensor and the third detection sensors are changed corresponding to the film-thickness direction of the mask; and
a second moving mechanism which moves the second focusing lens in a direction of an optical axis of the second focusing lens to change a position of focusing between sites of the pattern in the second illumination area in the film-thickness direction of the mask and the images of the pattern obtained by the second detection sensor and the fourth detection sensor, such that the images of the pattern obtained by the second detection sensor and the fourth detection sensors are changed corresponding to the film-thickness direction of the mask.

16. A mask defect inspection apparatus, comprising:

an illumination optical system which illuminates a plurality of illumination areas including at least a first illumination area and a second illumination area different from each other of a mask on which a pattern is formed;

an objective lens facing the mask;

a first focusing lens which receives first illumination light from the first illumination area of the mask obtained through the objective lens;

a second focusing lens which receives second illumination light from the second illumination area of the mask obtained through the objective lens;

a first detection sensor which obtains an image of the pattern in the first illumination area of the mask based on the first illumination light received by the first focusing lens;

a second detection sensor which obtains an image of the pattern in the second illumination area of the mask based on the second illumination light received by the second focusing lens;

a third detection sensor which obtains the image of the pattern in the first illumination area of the mask based on the first illumination light received by the first focusing lens;

a fourth detection sensor which obtains the image of the pattern in the second illumination area of the mask based on the second illumination light received by the second focusing lens;

a first half-mirror which divides the first illumination light obtained through the first focusing lens into the first illumination light that travels toward the first detection sensor and the first illumination light that travels toward the third detection sensor;

a second half-mirror which divides the second illumination light obtained through the second focusing lens into the second illumination light that travels toward the second detection sensor and the second illumination light that travels toward the fourth detection sensor;

a first moving mechanism which moves the first focusing lens in a direction of an optical axis of the first focusing lens to change a position of focusing between sites of the pattern in the first illumination area in a film-thickness direction of the mask and the image of the pattern obtained by the first detection sensor, such that the image of the pattern obtained by the first detection sensor is changed corresponding to the film-thickness direction of the mask; and a second moving mechanism which moves the second focusing lens in a direction of an optical axis of the second focusing lens to change a position of focusing between sites of the pattern in the second illumination area in the film-thickness direction of the mask and the image of the pattern obtained by the second detection sensor, such that the image of the pattern obtained by the second detection sensor is changed corresponding to the film-thickness direction of the mask, wherein a distance between the first detection sensor to the first half-mirror and a distance between the third detection sensor to the first half-mirror are different from each other, and a distance between the second detection sensor to the second half-mirror and a distance between the fourth detection sensor to the second half-mirror are different from each other.

17. A mask defect inspection apparatus, comprising:

an illumination optical system which illuminates a plurality of illumination areas including at least a first illumination area and a second illumination area different from each other of a mask on which a pattern is formed;

an objective lens facing the mask;

a first focusing lens which receives first illumination light from the first illumination area of the mask obtained through the objective lens;

a second focusing lens which receives second illumination light from the second illumination area of the mask obtained through the objective lens;

a first detection sensor which obtains an image of the pattern in the first illumination area of the mask based on the first illumination light received by the first focusing lens;

a second detection sensor which obtains an image of the pattern in the second illumination area of the mask based on the second illumination light received by the second focusing lens;

a third detection sensor which obtains the image of the pattern in the first illumination area of the mask based on the first illumination light received by the first focusing lens;

a fourth detection sensor which obtains the image of the pattern in the second illumination area of the mask based on the second illumination light received by the second focusing lens;

a first half-mirror which divides the first illumination light obtained through the first focusing lens into the first illumination light that travels toward the first detection sensor and the first illumination light that travels toward the third detection sensor;

a second half-mirror which divides the second illumination light obtained through the second focusing lens into the second illumination light that travels toward the second detection sensor and the second illumination light that travels toward the fourth detection sensor;

a first sensor moving mechanism which moves the first detection sensor and the third detection sensor in a direction of an optical axis of the first detection sensor and in a direction of an optical axis of the third detection sensor to change a position of focusing between sites of the pattern in the first illumination area in a film-thickness direction of the mask and the images of the pattern obtained by the first detection sensor and the third detection sensor, such that the images of the pattern obtained by the first detection sensor and the third detection sensor are changed corresponding to the film-thickness direction of the mask; and a second sensor moving mechanism which moves the second detection sensor in a direction of an optical axis of the second detection sensor and the fourth detection sensor in a direction of an optical axis of the fourth detection sensor to change a position of focusing between sites of the pattern in the second illumination area in the film-thickness direction of the mask and the images of the pattern obtained by the second detection sensor and the fourth detection sensor, such that the images of the pattern obtained by the second detection sensor and the fourth detection sensor are changed corresponding to the film-thickness direction of the mask.

* * * * *